US00RE41291E

(19) United States
(12) Reissued Patent
Viertio-Oja et al.

(10) Patent Number: US RE41,291 E
(45) Date of Reissued Patent: Apr. 27, 2010

(54) CLOSED LOOP DRUG ADMINISTRATION METHOD AND APPARATUS USING EEG COMPLEXITY FOR CONTROL PURPOSES

(75) Inventors: Hanna E. Viertio-Oja, Espoo (FI); Emmanuel-S Cohen-Laroque, Archamps (FR)

(73) Assignee: GE Healthcare Finland Oy, Helsinki (FI)

(21) Appl. No.: 11/232,411

(22) Filed: Sep. 21, 2005

Related U.S. Patent Documents

Reissue of:
(64) Patent No.: 6,631,291
Issued: Oct. 7, 2003
Appl. No.: 09/861,878
Filed: May 21, 2001

U.S. Applications:
(60) Provisional application No. 60/291,873, filed on May 18, 2001.

(51) Int. Cl.
*A61B 5/04* (2006.01)

(52) U.S. Cl. ..... 600/544; 600/546
(58) Field of Classification Search ..... 600/544, 600/545, 546
See application file for complete search history.

(56) References Cited

U.S. PATENT DOCUMENTS

| | | | |
|---|---|---|---|
| 2,690,178 | A | 9/1954 | Bickford |
| 4,417,590 | A | 11/1983 | Smith et al. |
| 4,421,122 | A | 12/1983 | Duffy |
| 4,533,346 | A | 8/1985 | Cosgrove, Jr. et al. |
| 4,705,049 | A | 11/1987 | John |
| 4,753,246 | A | 6/1988 | Freeman |
| 4,907,597 | A | 3/1990 | Chamoun |
| 5,010,891 | A | 4/1991 | Chamoun |
| 5,109,862 | A | 5/1992 | Kelen et al. |
| 5,320,109 | A | 6/1994 | Chamoun et al. |
| 5,458,117 | A | 10/1995 | Chamoun et al. |
| 5,474,082 | A | 12/1995 | Junker |

(Continued)

FOREIGN PATENT DOCUMENTS

| | | | |
|---|---|---|---|
| GB | 2113843 | * | 8/1983 |
| GB | 2113846 | | 8/1983 |
| WO | WO-97/34648 | | 9/1997 |
| WO | WO-98/10701 | | 3/1998 |
| WO | WO-02/32305 | | 4/2000 |

OTHER PUBLICATIONS

Closed–loop controlled administration of propofol using bispectral analysis, E. Mortier et al.; 1999 Anaesthesia, 1998, vol. 53, pp. 749–754.

(Continued)

*Primary Examiner*—Alfred Basichas
(74) *Attorney, Agent, or Firm*—Andrus, Sceales, Starke & Sawall, LLP

(57) ABSTRACT

A closed loop method and apparatus for controlling the administration of an hypnotic drug to a patient. Electroencephalographic (EEG) signal data is obtained from the patient. At least one measure of the complexity of the EEG signal data is derived from the data. The complexity measure may comprise the entropy of the EEG signal data. The EEG signal data complexity measure is used as the feedback signal in a control loop for an anesthetic delivery unit to control hypnotic drug administration to the patient in a manner that provides the desired hypnotic level in the patient. An EEG signal complexity measure obtained from the cerebral activity of the patient can be advantageously used in conjunction with a measure of patient electromyographic (EMG) activity to improve the response time of hypnotic level determination and of the feedback control of drug administration. A pharmacological transfer function may be used, along with pharmacokinetic and pharmacodynamic models.

50 Claims, 5 Drawing Sheets

U.S. PATENT DOCUMENTS

| | | | | | |
|---|---|---|---|---|---|
| 5,566,678 | A | | 10/1996 | Cadwell | |
| 5,579,774 | A | | 12/1996 | Miller et al. | |
| 5,769,793 | A | | 6/1998 | Pincus et al. | |
| 5,816,247 | A | | 10/1998 | Maynard | |
| 5,846,208 | A | | 12/1998 | Pichlmayr et al. | |
| 5,857,978 | A | | 1/1999 | Hively et al. | |
| 5,995,868 | A | | 11/1999 | Dorfmeister et al. | |
| 6,016,444 | A | | 1/2000 | John | |
| 6,061,593 | A | | 5/2000 | Fischell et al. | |
| 6,067,467 | A | | 5/2000 | John | |
| 6,117,066 | A | | 9/2000 | Abrams et al. | |
| 6,128,094 | A | * | 10/2000 | Smith | 358/1.15 |
| 6,138,668 | A | * | 10/2000 | Patton et al. | 128/200.14 |
| 6,594,524 | B2 | | 7/2003 | Esteller et al. | |
| 6,678,548 | B1 | * | 1/2004 | Echauz et al. | 600/544 |
| 6,731,975 | B1 | | 5/2004 | Viertio-Oja et al. | |
| 2002/0061540 | A1 | * | 5/2002 | Grass et al. | 435/7.1 |

OTHER PUBLICATIONS

New Method to Determine Depth of Anesthesia From EEG Measurements, H. E.. Viertiö–Oja et al., Journal of Clinical Monitoring and Computing, vol. 16, No. 1, Jan. 2000, p. 60.

Entropy of the EEG Signal is a Robust Index for Depth of Hypnosis, Hanna E. Viertiö–Oja et al., 2000 ASA Meeting Abstracts, pp. 1–2.

Approximate Entropy as an Electroencephalographic Measure of Anesthetic Drug Effect During Desflurane Anesthesia, Jorgen Bruhn, M.D., et al., Anesthesiology, vol. 92, No. 3, Mar. 2000, pp. 715–726.

A Primer for EEG Signal Processing in Anesthesia, Ira J. Rampil, M.S., M.D., Anesthesiology, vol. 89, No. 4, Oct. 1998, pp. 980–1002.

Increasing isoflurane concentration may cause paradoxical increases in the EEG bispectral index in surgical patients, O. Detsch et al., British Journal of Anaesthesia 2000, 84(1): pp. 33–37.

Stochastic Complexity Measures for Physiological Signal Analysis, I.A. Rezek et al., IEEE Transactions on Biomedical Engineering, vol. 45, No. 9, Sep. 1998, pp. 1186–1191.

Predicting movement during anaesthesia by complexity analysis of electroencephalograms, X.–S. Zhang et al., Medical and Biological Engineering & Computing, 1999, vol. 37, pp. 327–334.

A Regularity Statistic for Medical Data Analysis, Steven M. Pincus, PhD, et al., Journal of Clinical Monitoring, vol. 7, No. 4, Oct. 1991, pp. 335–345.

On the Complexity of Finite Sequences, Abraham Lempel, et al., IEEE Transactions on Information Theory, vol. IT–22, No. 1, Jan. 1976, pp. 75–81.

The effects of nitrous oxide and ketamine on the bispectral index and 95% spectral edge frequency during propofol–fentanyl anaesthesia, K. Hirota et al., European Journal of Anaesthesiology 1999, vol. 16, pp. 779–783.

Electromyographic Activity Falsely Elevates the Bispectral Index, Jörgen Bruhn, M.D. et al., Anesthesiology, vol. 92, No. 5, May 2000, pp. 1485–1487.

Relationship between calculated blood concentration of propofol and electrophysiological variables during emergence from anaesthesia: comparison of bispectral index, spectral edge frequency, median frequency and auditory evoked potential index, M. Doi et al., British Journal of anaesthesia 1997, vol. 78, pp. 180–184.

Phamacokinetics and Phamacodynamics of Propofol Infusions during General Anaesthesia, Audrey Shafer, M.D. et al., Anesthesiology, vol. 69, pp. 348–356, 1988.

Electroencephalogram Approximate Entropy Correctly Classifies the Occurrence of Burst Suppression Pattern as Increasing Anesthetic Drug Effect, Jörgen Bruhn, M.D. et al., Anesthesiology vol. 93, No. 4, Oct. 2000, pp. 981–985.

*Onset of Propofol–Induced Burst Suppression May Be Corrected Detected as Deepening of Anaesthesia by Approximate Entropy, But Not by Bispectral Index*, Br. J. Anaesth. Sep. 2001; 87(3):505–7 by Bruhn Jr., Bouillon, T.W., Shafer, S.L..

*Theoretical Electroencephalogram Stationary Spectrum for a White–noise–driven Cortex: Evidence for a General Anesthetic–Induced Phrase Transition*, Moira I. Steyn–Ross and D.A. Steyn–Ross et al. 1999 The American Physical Society, Physical Review E, vol. 60, No. 6, Dec. 1999, pp. 7299–7310.

*Development Equations for the Electroencephalogram*, E.R. John, H. Ahn, L. Prichep, T. Trepetin, D. Brown, and H. Kaye, Science, 10980, 210: 1255–1258.

*Quantification of EEG Irregularity by Use of the Entropy of the Power Spectrum*, T. Inouye, K. Shinosaki, H. Sakamotor, S. Toi, S. Ukai, A. Iyama, Y. Katsuda and M. Hirano, Electroencephalography and Clinical Neurophysiology, 70 (1191) 204–210.

Amendment dated Jan. 10, 2006 filed in European Patent Application 2727903.3.

International Search Report in WO 02/094099—also use din European Patent Application 2727903.3.

European Patent Office Action of Jun. 12, 2006.

European Amendment dated Dec. 12, 2006.

European Patent Office Action of Aug. 27, 2007.

Office Action of European Patent Office, Mar. 21, 2005.

U.S. Appl. No. 09/688,891, Viertiö–Oja et al., filed Oct. 2000.*

* cited by examiner

CLOSED LOOP DRUG ADMINISTRATION METHOD AND APPARATUS USING EEG COMPLEXITY FOR CONTROL PURPOSES

Matter enclosed in heavy brackets [ ] appears in the original patent but forms no part of this reissue specification; matter printed in italics indicates the additions made by reissue.

CROSS REFERENCE TO RELATED APPLICATION

The present application claims the priority of U.S. provisional application 60/291,873, filed May 18, 2001.

BACKGROUND OF THE INVENTION

The present invention is directed to a method and apparatus for controlling the administration of an hypnotic drug in "closed loop" fashion.

An hypnotic drug may comprise an anesthetic agent and the hypnotic state induced in a patient by the administration of such a drug in one of anesthetization. An hypnotic drug typically acts on the brain to produce a lessening or loss of consciousness in the patient. The extent to which the patient is anesthetized is often termed the "hypnotic level" or "depth of anesthesia." In the present invention, the existing hypnotic level, or depth of anesthesia, in the patient is sensed and used to control the hypnotic drug administration to the patient in the manner of a closed loop, or feedback, regulator to achieve and maintain a desired level in the patient.

More particularly, the present invention employs the complexity of electroencephalographic (EEG) data obtained from the patient as a sensed indication of the hypnotic level of the patient for use in controlling hypnotic drug administration. The use of such an indication provides closed loop control of drug administration that is based on an accurate assessment of the hypnotic condition of the patient and one that is highly responsive to changes in that condition. Such an indication can be made rapidly responsive to changes in the hypnotic condition of the patient.

Hypnotic drugs, or anesthetic agents, are administered by inhalation or intravenously. When administration is by inhalation, the anesthetic agent comprises a volatile liquid that is vaporized in a vaporizer. The vaporized anesthetic agent is entrained in breathing gases for the patient. The concentration of the anesthetic agent supplied by the vaporizer is determined by the anesthesiologist by manipulating appropriate controls on the vaporizer. The concentration of anesthetic agent in the lungs of the patient may be measured by measuring the amount of anesthetic agent contained in the breathing gases exhaled by the patient at the end of the exhalation phase of the respiratory cycle, i.e. the end tidal concentration ($ET_{conc}$). Typical inhaled anesthetic agents are sevoflurane, enflurane, and desflurane, among others.

In a simple form, intravenous administration of an hypnotic drug may employ a syringe that injects the drug into a vein of the patient. For extended administration, a motor driven syringe or a motor driven infusion pump may be employed. A commonly used, intravenously administered, anesthetic agent is propofol.

In addition to hypnosis, high quality anesthesia must also consider loss of sensation (analgesia), muscle relaxation, suppression of the autonomous nervous system, and blockage of the neuro muscular function. This may require administration of a number of different drugs via the same or different routes. Further, different hypnotic drugs and/or different administration routes may be used at different stages of an anesthetization or a medical procedure. For example, hypnosis may be introduced by an intravenously administered drug and maintained by an inhaled drug.

In the process by which a drug, including a hypnotic drug, takes its effect in the body, two aspects are important: pharmacokinetics and pharmacodynamics. [Pharmacokinetics] *Pharmacodynamics* deals with the effect of the body on the drug, such as the body's absorption, distribution or diffusion, metabolism, and excretion of the drug. Pharmacokinetics describes how the drug is distributed in the course of time from the site of delivery to different parts of the body and to a particular organ in which the drug is supposed to have its effect.

For use in the study of drugs, the determination of dosages, and the like, mathematical models have been developed for the pharmacokinetics of a drug. Because of the complexity of the physiology of the body, the models are typically based on theoretical compartments, such as plasma, fat, or the brain. Pharmacokinetic models typically allow for consideration of anthropometric data, such as patient height, weight, age, sex, etc. Pharmacokinetic models are available for hypnotic drugs, or anesthetic agents, including propofol, based on two or more different compartments. See Shafer, et al. Anesthesiology, 1998; 69:348–356 describing a two compartment model for propofol.

When a specific effect of a drug can be directly or indirectly measured, such data can be used to define a pharmacodynamic model of the drug with respect to its concentration at the site at which it is effective, i.e. effect-site concentration. Such models may also use anthropometric data. For hypnotic drugs the effect is the hypnotic state of the patient and the effect-site in the brain.

In a broad sense, all hypnotic drug administration is of a controlled loop nature. In a basic form, an anesthesiologist administers such a drug to a patient, observes the state of the patient resulting from the administration of the drug, and then maintains or alters the dose based on his/her observations. However, in a more specific sense, reflecting recent work in the field of anesthesia, closed loop control relates to the sensing of the hypnotic state of the patient by some form of instrumentation and automatically controlling the administration of the drug responsive to a feedback signal from the instrumentation. The term is used herein in the more specific sense.

The interest in closed loop control is posited, at least in part, on a desire to accurately establish the hypnotic level or depth of anesthesia of the patient. If the anesthesia is not sufficiently deep, the patient may maintain or gain consciousness during a surgery, or other medical procedure, resulting in an extremely traumatic experience for the patient, anesthesiologist, and surgeon. On the other hand, excessively deep anesthesia reflects an unnecessary consumption of hypnotic drugs, most of which are expensive. Anesthesia that is too deep requires increased medical supervision during the surgery recovery process and prolongs the period required for the patient to become completely free of the effects of the drug.

Rapidity is another desirable feature of an hypnotic drug administration control system. Fast response is particularly desirable should the patient approach consciousness since, as noted above, unexpected emergence is to be avoided, but is rendered more likely as excessively deep anesthesia is avoided.

A closed loop hypnotic drug delivery system has been described using the bispectral index as a control parameter.

See Mortier E., et al. Anesthesia, 1998, August; 53 (8):749–754. See also published European Patent Application No. EP 959,921 to authors of this article. The bispectral index is proprietary to Aspect Medical Systems of Farmingham, Mass. and is described in one or more of the following U.S. Pat. Nos.: 4,907,597; 5,101,891; 5,320,109; and 5,458,117. The bispectral index is an effort to form a single variable, termed the bispectral index (BIS), that correlates behavioral assessments of sedation and hypnosis over a range of anesthesia for several hypnotic drugs.

The bispectral index comprises three components that are combined in various ways to provide an indication over a range of hypnotic levels from light sedation to deep anesthesia. See Ira R. Rampil, "A Primer for EEG Signal Processing in Anesthesia", Anesthesiology 89 (1998), 980–1002. See also U.S. patent application, Ser. No. 09/688,891 to an inventor named herein and another, assigned to a common assignee, also containing a description of this index.

In order to compute a BIS value, measured EEG data over a period of fifteen seconds is used. During anesthesia, the level of painful stimulation can vary drastically and cause rapid changes in the hypnotic level of the patient, i.e. wake the patient up. Because of the time required to compute a BIS value, the bispectral index may not be sufficiently rapid to warn the anesthesiologist that this is occurring. Also, the bispectral index is contaminated by electromyographic (EMG) activity which may lead to misjudgment of the hypnotic level of a patient. See Bruhn J., et al., Anesthesiology 2000; 92:1485–7. Certain paradoxical behavior of the bispectral index (BIS) not connected to EMG has also been reported; see Detsch O. et al., British Journal of Anesthesia 84 (1):33–7 (2000); Hirota K. et al., Eur J Anaesth 1999, 16, 779–783.

Another approach to closed loop or feedback control of hypnotic drug administration is disclosed in published International Patent Appln. WO 98/10701 by Mantzaridis, et al. In the technique of the patent, the patient is fitted with headphones and is subjected to noise in the form of "clicks" of one ms duration at a frequency of 6.9 Hz. The auditory evoked potential (AEP) resulting from this stimulation, and more particularly, the alteration of the delay between the auditory stimulus and the auditory stem response in the brain is used in this method to evaluate the level of hypnosis of a patient during anesthesia. While an AEP index has been shown to distinguish between the conscious and unconscious states of a patient in an accurate manner, the correlation with drug concentration is not as good and has been reported as poorer than that for the bispectral index. See Doi M, et al., Br J Anaesth. 1997, February; 78(2):180–4. The auditory response does not persist to the lowest hypnotic levels, restricting the range of measurement. This tends to lessen the utility of the AEP index for use in closed loop hypnotic drug administration. Also, the technique requires placing earphones on the patient and is limited to patients having adequate hearing.

U.S. Pat. No. 6,016,444 to E. R. John, describes another method using information extracted from EEG signal data to control a closed-loop drug delivery system. The parameters mentioned include EEG spectral powers measured in different frequency ranges and the spectral edge frequencies, below which are found, for example, 50% or 90% of the total power spectrum. In addition to the EEG spectrum derived parameters, the method also uses brain wave evoked responses, such as brain stem or cortical auditory evoked responses, which may bear a correlation to anesthesia level. Electrodes are applied to the front and back of the scalp and the method essentially compares the derived features between these locations using covariance matrices. After the patient has been anesthetized and when he/she has obtained the plane of anesthesia desired by the anesthesiologist, a form of calibration procedure called "self-normalization" is carried out. The plane of anesthesia is determined by clinical signals observed by the anesthesiologist. After self-normalization, the system tries to maintain the anesthetic level of the patient established during that procedure as the set point.

The need for the self-normalization procedure presents a disadvantage to this procedure in that the anesthesiologist may forget to carry it out or carry it out at the wrong plane of anesthesia. In the time period required for the procedure, which according to the patent preferably lasts for 60 seconds, the condition of the patient may change. Also, there is no published evidence that the particular EEG-derived parameters chosen for measurement correlate very well with hypnotic levels.

BRIEF SUMMARY OF THE INVENTION

It is, therefore, an object of the present invention to provide an improved method and apparatus for controlling the administration of an hypnotic drug to a patient in closed loop fashion that employs an accurate and highly responsive indication of the hypnotic condition of the patient, thereby to improve the administration of the drug. The indication used in the present invention can be made rapidly responsive to changes in the hypnotic condition of the patient. This is particularly advantageous in alerting an anesthesiologist that the patient may be emerging from an anesthetized state to a conscious state.

It is a further object of the present invention to provide a closed loop control method and apparatus which is capable of operating over a wide range of hypnotic conditions in the patient ranging from no hypnosis, i.e. consciousness, to deep hypnosis or anesthesia.

The method and apparatus of the present invention is simple to set up, employing a simple array of electrodes on the head of the patient. No self-normalization procedure as required in earlier disclosed techniques, is required with the technique of the present invention.

Briefly, in the present invention, electroencephalographic (EEG) signal data is obtained from the patient. For this purpose, one or more pairs of biopotential electrodes may be applied to the forehead of the patient. At least one measure of the complexity of the EEG signal data is derived from the data. The complexity measure of the EEG signal data may comprise the entropy of the EEG signal data. An EEG signal complexity measure obtained from the cerebral activity of the patient can be advantageously used in conjunction with a measure of patient electromyographic (EMG) activity resulting from the muscle activity of the patient to improve the response time of hypnotic level determination and of the feedback control of drug administration. The EEG signal data complexity measure is used in as the feedback signal in a control loop for an anesthetic delivery unit to control hypnotic drug administration to the patient in a manner that provides the desired hypnotic level in the patient.

A plurality of EEG signal data complexity measures may be used in determining the hypnotic level of the patient, if desired.

To improve the control of hypnotic drug administration, the present invention may employ a transfer function relating to the pharmacological effects of the drug in the patient and the manner, or other characteristics of, its administration. Pharmacokinetic and pharmacodynamic models may be employed in establishing the transfer function.

The control of drug administration provided by the present invention may be improved by the use of additional data obtained from the patient, such as his/her cardiovascular characteristics or the end tidal concentration of volatile hypnotic drugs.

Information pertinent to the anesthetization of the patient, such as patient characteristics, hypnotic drug type, particular medical procedure and physician, may be inputted or stored for use in carrying out the control of drug administration. Information generated during course of an anesthetization may also be employed in controlling the administration of the hypnotic drug to the patient.

Various other features, objects, and advantages of the invention will be made apparent from the following detailed description and the drawings.

DETAILED DESCRIPTION OF THE INVENTION

Figure 1:
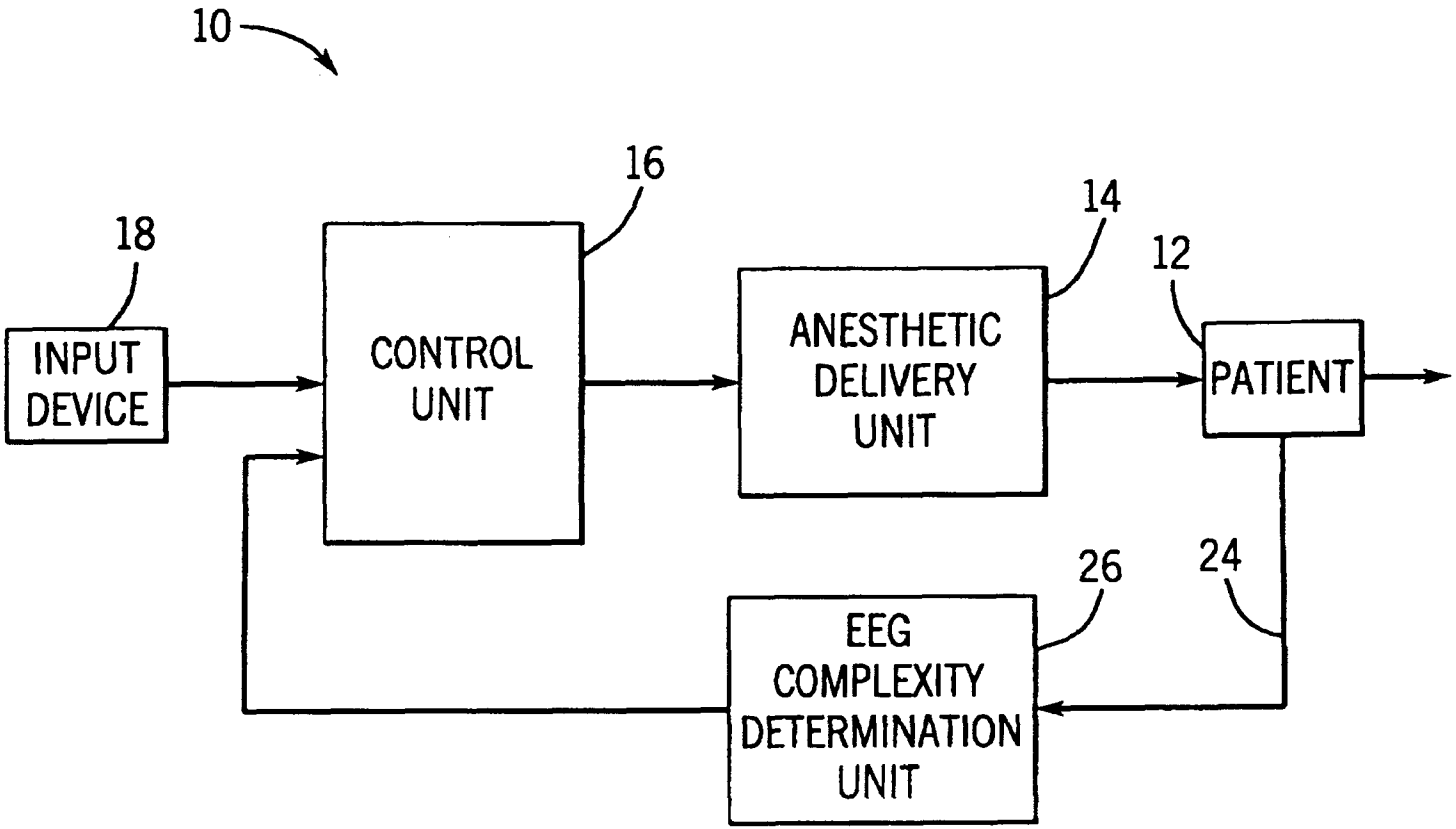
FIG. 1 is a schematic diagram showing one embodiment of a closed loop drug administration control using EEG complexity for control purposes.

In the present invention, a quantification of the complexity of the EEG signals obtained from the patient is used to determine his/her hypnotic level and, in turn, to control the administration of a hypnotic drug to the patient in a closed loop fashion. This approach is based on the premise that neuronal systems, such as those of the brain, have been shown to exhibit a variety of non-linear behaviors so that measures based on the non-linear dynamics of the highly random EEG signal allow direct insight into the state of the underlying brain activity. EEG biopotential signals are obtained from electrodes applied to the head of the patient.

There are a number of concepts and analytical techniques directed to the complex nature of random and unpredictable signals. One such concept is entropy. Entropy, as a physical concept, describes the state of disorder of a physical system. When used in signal analysis, entropy addresses and describes the complexity, unpredictability, or randomness characteristics and information content of a signal. In a simple example, a signal in which sequential values are alternately of one fixed magnitude and then of another fixed magnitude has an entropy of zero, i.e. the signal is totally predictable. A signal in which sequential values are generated by a random number generator has greater complexity and a higher entropy.

Applying the concept of entropy to the brain, the premise is that when a person is awake, the mind is full of activity and hence the state of the brain is more nonlinear, complex, and noise like. Since EEG signals reflect the underlying state of brain activity, this is reflected in relatively more "randomness" or "complexity" in the EEG signal data, or, conversely, in a low level of "order." As a person falls asleep or is anesthetized, the brain function begins to lessen and becomes more orderly and regular. As the activity state of the brain changes, this is reflected in the EEG signals by a relative lowering of the "randomness" or "complexity" of the EEG signal data, or conversely, increasing "order" in the signal data. When a person is awake, the EEG data signals will have higher entropy and when the person is asleep the EEG signal data will have a lower entropy.

With respect to anesthesia, an increasing body of evidence shows that EEG signal data contains more "order", i.e. less "randomness", and lower entropy, at higher concentrations of an hypnotic drug, i.e. a lower hypnotic level or greater depth of anesthesia, than at lower concentrations. At a lower concentration of hypnotic drug, the EEG signal has higher entropy. This is due, presumably, to lesser levels of brain activity in the former state than in the latter state. See "Stochastic complexity measures for physiological signal analysis" by I. A. Rezek and S. J. Roberts in IEEE Transactions on Biomedical Engineering, Vol. 4, No. 9, September 1998 describing entropy measurement to a cut off frequency of 25 Hz and Bruhn J, et al. "Approximate Entropy as an Electroencephalographic Measure of Anesthetic Drug Effect during Desflurane Anesthesia", Anesthesiology, 92 (2000), pgs. 715–726 describing entropy measurement in a frequency range of 0.5 to 32 Hz. See also Viertiö-Oja H, et al. "New method to determine depth of anesthesia from EEG measurement" in J. Clin. Monitoring and Comp. Vol. 16 (2000) pg. 60 which reports that the transition from consciousness to unconsciousness takes place at a universal critical value of entropy which is independent of the patient. See also Zhang XS et al., Med. Bio. Eng. Comput. 1999, 37:327–34.

In sum, the following can be said. First, certain forms of entropy have generally been found to behave consistently as a function of hypnotic or anesthetic depth. See Bruhn J, et al. Anesthesiology 92 (2000) 715–26; Anesthesiology 93 (2000) 981–5 and Viertiö-Oja H, et al. "Entropy of EEG signal is a robust index for depth of hypnosis", Anesthesiology 93 (2000) A, pg. 1369. This warrants consideration of entropy as a natural and robust choice to characterize levels of hypnosis. Also, because entropy correlates with depth of anesthesia at all levels of anesthesia, it avoids the need to combine various subparameters as in the bispectral index (BIS). Second, it has been found that the transition from consciousness to unconsciousness takes place at a critical level of entropy which is independent of the patient. See Viertiö-Oja H, et al. in J. Clin. Monitoring and Computing, Vol. 16 (2000) pg. 60. Thirdly, and of particular practical significance, recovery of a patient toward consciousness from anesthesia can often be predicted by a rise of entropy toward the critical level.

A number of techniques and associated algorithms are available for quantifying signal complexity, including those based on entropy, as described in the Rezek and Roberts article in IEEE Transactions on Biomedical Engineering. One such algorithm is that which produces spectral entropy for which the entropy values are computed in frequency space. Another algorithm provides approximate entropy which is derived from the Kolmogorov-Sinai entropy formula and computed in Taken's embedding space. See Steven M. Pincus, Igor M. Gladstone, and Richard A. Ehrenkranz, "A regularity statistic for medical data analysis", J. Clin. Monitoring 7 (1991), pgs. 335–345. A program for computing approximate entropy is set out in the Bruhn et al., article in Anesthesiology. The spectral entropy and approximate entropy techniques have found use in analyzing the complexity of EEG signals.

Another technique for non-linear analysis of highly random signals is expressed in Lempel-Ziv complexity in which the complexity of a string of data points is given by the number of bytes needed to make the shortest possible computer program which is able to generate the string. See Abraham Lempel and Jacob Ziv, "On the complexity of finite sequences", IEEE Trans., IT-22 (1976), pgs. 75–81.

A still further approach that may be applied to EEG signal analysis is fractal spectrum analysis based on chaos theory. In fractal spectrum analysis, the EEG signal is divided into a harmonic component and a fractal component. The harmonic component includes the simple frequencies whereas the fractal component contains the part which is invariant under scaling in time. It has been found that the fractal exponent Beta which corresponds to the frequency power law $1/f^{\beta}$ increases consistently in the course of deepening anesthesia. See Vierti0-Oja, H. et al. in J. Clinical Monitoring and Computing, Vol. 16 (2000), pg. 16.

The use of spectral entropy to characterize the amount of complexity or disorder in an EEG signal is deemed advantageous because of its computational simplicity. The use of spectral entropy to obtain a diagnostic index indicative of the depth of anesthesia of hypnotic level of a patient is described in detail in the aforesaid U.S. patent application 09/688,891 which is incorporated herein by reference in its entirety.

The complexity measurement derived from EEG signal data can be combined with a more rapidly obtainable measure derived from electromyographic (EMG) signals. EMG signals result from the activity of the muscles and exist as long as the muscles are not paralyzed. With the measurement of electromyographic (EMG) activity contained in the biopotentials from electrodes on the forehead of the patient, as the level of anesthesia approaches inadequacy, a painful stimulus to the patient causes a contraction of the frontalis muscle (frowning) which can be detected as peaks in EMG signal amplitude. This reaction can often be observed substantially before the pain eventually brings the patient to consciousness. EMG signals can thus provide an early warning sign to the anesthesiologist to increase the administration of hypnotic drug(s) in order to prevent consciousness and awareness during surgery. The measure derived from the EMG signals may comprise spectral power data.

Both the EEG and EMG signals are typically obtained from the same set of electrodes applied, for example, to the forehead of the patient so that the signals from the electrodes contain both types of data. The EEG signal component dominates the lower frequencies (up to about 30 Hz) contained in the biopotentials existing in the electrodes and EMG signal component dominates the higher frequencies (about 50 Hz and above).

Importantly, because of the higher frequency of the EMG signals, the sampling time can be significantly shorter than that required for the lower frequency EEG signals. This allows the EMG data to be computed more frequently so that a combined EEG-EMG diagnostic indicator of hypnotic level or depth of anesthesia can quickly indicate changes in the state of the patient.

In one approach to providing such a diagnostic index, the EEG signals and the EMG signals can be separately analyzed and thereafter combined into the diagnostic index or indicator. As noted above, because of the celerity with which changes in the anesthetic state of the patient can be determined from the EMG signals, the overall index can quickly inform the anesthesiologist of changes in the state of the patient. For example, the response time for computing the hypnotic level of the patient from the complexity of the EEG signal is approximately 5–30 seconds whereas the data derived from the EMG signal and the diagnostic index can be fully updated every 0.5 seconds.

In another approach, the spectral range of the complexity computations, i.e. entropy computations, is widened to extend into the EMG range. Thus, the spectral range over which the complexity computations are carried out to provide an indicator may extend from some lower frequency of, for example 0.5 to 7 Hz, up to a frequency above 32 Hz. To filter out power line interference, the spectral range may be divided into bands with the elimination of frequencies around 50, 60 Hz and 100, 120 Hz. For example, in an embodiment in which the spectral range extends to approximately 150 Hz, a lower frequency band (0.5–47 Hz) will contain mostly EEG activity while two upper bands (63–97 Hz and 123–147 Hz) will include primarily EMG activity. The use of a widened frequency range does not require a division of the spectrum into two segments as does the first approach because all components in the widened frequency range are treated in the same manner. And, any boundary within the spectral range would be artificial since the frequency bands for the EEG and EMG signals are overlapping.

Further, the complexity measurement obtained in this second approach can be updated as often as is permitted by the higher frequencies of the EMG signals in the widened spectral range of the complexity computation. This will provide a very current indication to the anesthesiologist of the depth of anesthesia of the patient.

The indicator obtained from the signal complexity computation over the widened spectral range can be used in conjunction with a complexity measurement obtained only from the EEG portions of the frequency spectrum to provide useful information to the anesthesiologist regarding what portion of the indicator comes from cerebral activity and what portion comes from muscle activity. This is particularly important in cases in which muscle tension is enhanced for some reason. An example that is frequently encountered is with opioid anesthesia that is often used in heart operations. The extensive use of opioids has the side effect of high muscle rigidity that persists after loss of consciousness. If the BIS is used, this results in misleadingly high values of the BIS. Distinction of the complexity measurement obtained only from the EEG portions of the frequency spectrum from the signal complexity over the widened spectral range shows this situation clearly.

FIG. 1 schematically shows control apparatus 10 for supplying an hypnotic drug to patient 12. For control purposes, apparatus 10 employs EEG signal data complexity as an indication of the hypnotic level existing in the patient. As used herein, the term "EEG signal data" may be taken to mean data obtained from cerebral activity of the patient, i.e. so-called "pure EEG signals", either without or with data obtained from muscle activity, i.e. EMG signals.

The hypnotic drug may be supplied to patient 12 by anesthesia delivery unit 14. If the drug is administered intravenously anesthetic delivery unit 14 may comprise a motor driven infusion pump. For hypnotic drugs administered by inhalation, anesthesia delivery unit 14 is typically a vaporizer. As noted above, it is common to use both types of hypnotic drugs and differing anesthetic delivery units in the course of an anesthetization. The amount of hypnotic drug delivered by anesthetic delivery unit 14 is controlled by control unit 16, typically by controlling its infusion or administration rate.

In FIG. 1, an input signal to control apparatus 10 is provided by input device 18 operated by the anesthesiologist. For example, the anesthesiologist may establish a value corresponding to the hypnotic level to be achieved in patient 12 and the input device would provide an appropriate input signal to control unit 16. Or, the anesthesiologist may input a value corresponding to a specific desired dosage, if for example control 10 is operated in an open loop fashion. Input device 18 or control unit 15 may establish related criteria such as the minimum and maximum dosages or defined delivery rates of hypnotic drug to be delivered by control 10.

Figure 2:
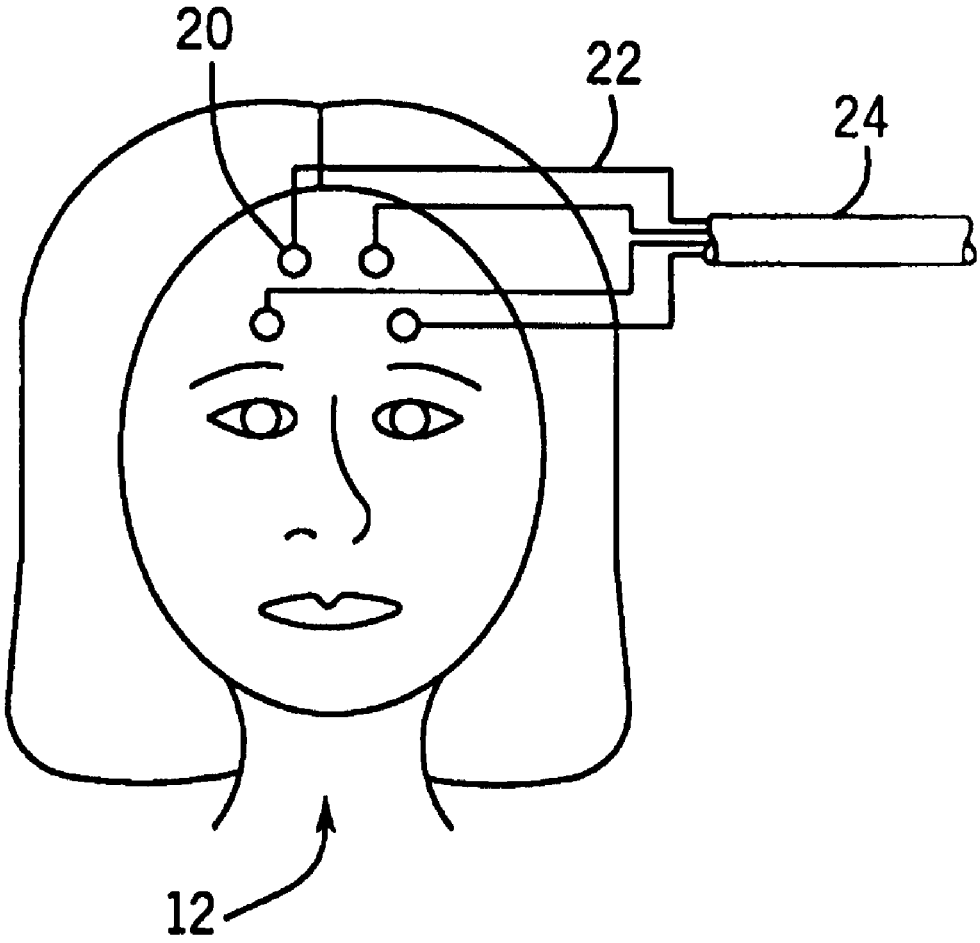
FIG. 2 shows one form for the placement of electrodes on a patient.

To determine the hypnotic state existing in patient 12, electrodes 20 may be applied to the forehead of patient 12 as shown in FIG. 2. Electrodes 20 receive electroencephalographic (EEG) signals from patient 12. The electrodes also receive electromyographic (EMG) signals from the forehead of patient 12. Electrodes 20 are connected to conductors 22 which may be formed into cable 24.

Cable 24 is connected to EEG complexity determination unit 26. Unit 26 includes a protection circuit which is operative in the event the patient is subjected to electro-surgery or cardiac defibrillation, an analog digital converter, and a bandpass filter. Unit [24] *26* also contains one or more computational elements, such as a microprocessor, that performs artifact detection and removal and determines the spectral entropy or other characterization of the amount of complexity or disorder in the EEG signal obtained from electrodes 20, as well as spectral power data derived from the EMG signal data obtained from the electrodes, thereby to provide EEG signal data.

The output of EEG complexity determination unit 26 comprises a diagnostic index or other value indicative of the complexity or disorder of the EEG signal data. As noted above, it is deemed preferable for reasons of reducing response times, particularly in sensing the emergence of the patient from the hypnotic state, to incorporate data from EMG signals in such a diagnostic index or value. It may also be advantageous to provide more than one index. For example, indices in which signal complexities have has been computed over different frequency ranges may be used. The output from EEG complexity determination unit is provided to a further input of control unit 16 as shown in FIG. 1 to complete a control loop in control 10.

Figure 1A:
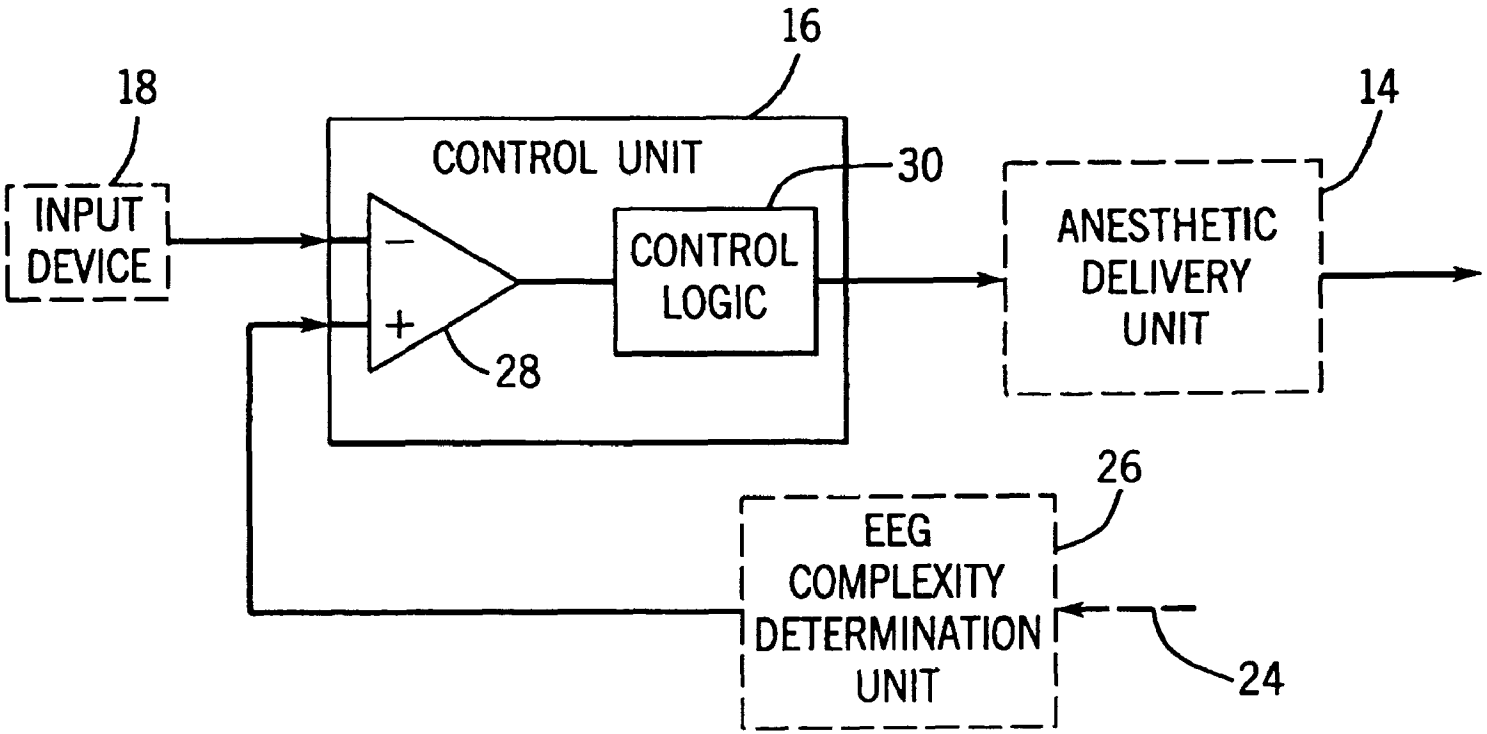
FIG. 1A is partial schematic diagram of a component of the control shown in FIG. 1.

In a simple embodiment of the invention shown in FIG. 1, control [logic] *unit* 16, may be seen as a comparator 28, as shown in FIG. 1A. Comparator 28 compares the reference signal generated by input device [16] *18* with the feedback signal provided by EEG complexity determination unit [24] *26* and provides an output signal corresponding to the difference between the two inputs. This output signal may be applied to control logic or signal processor 30, the output of which forms the output signal to anesthetic delivery unit 14 for use in controlling the amount of hypnotic drug delivered to patient 12 and hence his/her hypnotic level.

The hypnotic level existing in patient 12, as ascertained by EEG complexity determination unit 26, is driven toward that corresponding to the input signal from input device 18 by the action of the control loop in control 10 in the well known manner of a closed loop or feedback regulator. The polarity of the reference and feedback inputs to comparator [26] *28* are shown in FIG. 1A to graphically connote this control action. Specifically, the closed loop control apparatus incorporating control unit 16 acts in a manner to drive the difference between the reference signal from input unit 18 and the feedback signal from EEG complexity determination unit 26, and hence the output signal from control unit 16, to zero. For example, and starting at a zero input signal difference and output signal condition, if the hypnotic level of the patient elevates, or moves towards consciousness, the complexity of the EEG signal data will increase, as will the input signal from complexity determination unit 26 to the positive input of comparator 28. This will produce a positive output from control unit 16 to anesthetic delivery unit 14, which may be taken as a symbolic indication that a greater quantity of hypnotic drug should be administered to patient 12 by anesthetic delivery unit 14 to restore the hypnotic level to a lower value. The greater amount of drug so delivered will decrease the hypnotic level in the patient and cause it to move toward that established by the reference signal from input device 18. The decrease in the hypnotic level also causes the input signal from complexity determination unit to decrease to restore the input signal difference to zero. The converse is true if the hypnotic level of the patient moves towards a greater state of unconsciousness. That is, as patient 12 moves to a greater degree of unconsciousness, the output signal from EEG complexity determination unit [24] *26* will decrease. When compared to the reference signal from input device [16] *18*, this will cause the output signal from comparator [26] *28* to assume a symbolic negative value, indicative of a reduction in the amount of hypnotic drug to be supplied to patient 12 from anesthetic delivery unit 14 thereby allowing the level of unconsciousness of the patient to rise back to the desired value.

Figure 3:
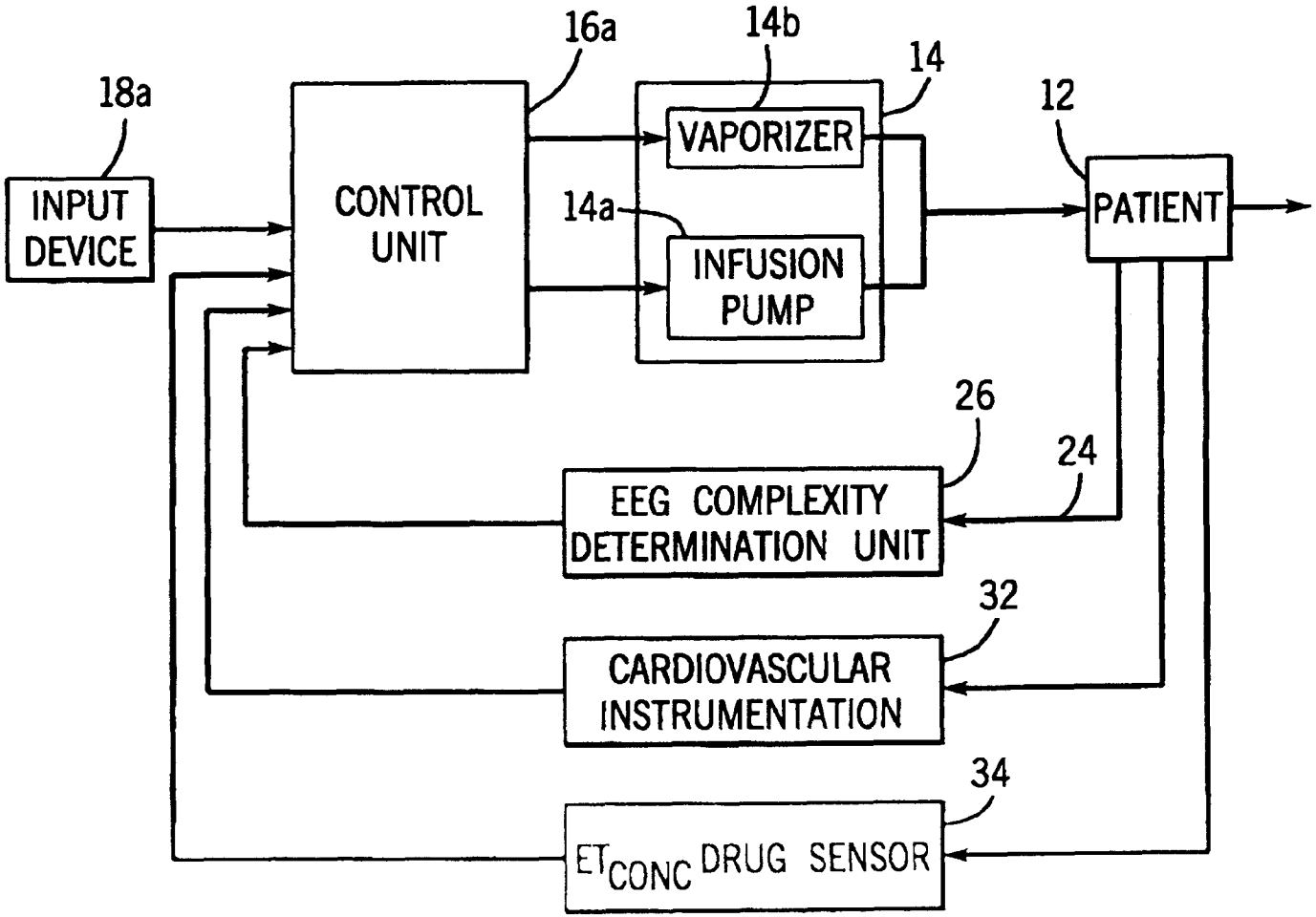
FIG. 3 is a schematic diagram showing a modification of the control in FIG. 1.

As shown in FIG. 3, to improve the administration of the hypnotic drug and to enhance patient safety, additional physiological data may be obtained from patient 12 for use in the operation of the closed loop control. For example, it is known that many, if not most of the drugs used in anesthesia, affect, sometimes severely, the cardiovascular status of the patient. Propofol is known to induce a drop of systemic blood pressure in patients, whereas desflurane can induce a significant increase in heart rate. This may have a significant impact on patients particularly sensitive to such changes of vital function such as elderly patients, critically ill patients, and diabetic patients. To this end, cardiovascular parameters, such as heart rate, blood pressure, blood oxygen saturation, and cardiac output, can be obtained by appropriate instrumentation 32 and supplied as a feedback signal to control unit 16a. Desired, or reference, values for these parameters may be inputted by an appropriate input device 18a, along with or separate from an hypnotic level reference values, to alter the output of control unit 16a to anesthetic delivery unit 14 so that the administration of the hypnotic drug to patient 12 is carried out in a manner to preserve these vital functions. The cardiovascular parameters may be used to alter the input signals provided to control unit 16a or a separate control loop responsive to desired and actual cardiovascular data may be provided inside of or outside of the control loop employing the EEG signal data complexity to, for example, limit the delivery rate of a drug or provide a specific combination of intravenous and volatile drugs.

Also as shown in FIG. 3, anesthetic delivery unit 14 may comprise an intravenous infusion pump 14a and a vaporizer 14b, for intravenously administered and inhaled hypnotic drugs, respectively. Pump 14a and vaporizer 14b may be controlled in coordinated fashion by control unit 16a.

As further shown in FIG. 3, when an inhaled hypnotic drug is administered to patient 12, as by use of vaporizer 14b, the end tidal drug concentration ($ET_{conc}$) exhaled by patient [10] *12* may be measured by sensor 34 and supplied as a feedback signal to control unit 16a to provide a feedback control that ensures that the amount of hypnotic drug received by the patient corresponds to that commanded by the input to vaporizer 14b from control unit 16a. The concentration of hypnotic drug in the end tidal breathing gases of the patient corresponds to the concentration in the lungs of the patient and, therefore to that in the breathing gases provided to patient 12 by vaporizer 14b and is thus useful as a feedback signal.

Figure 4:
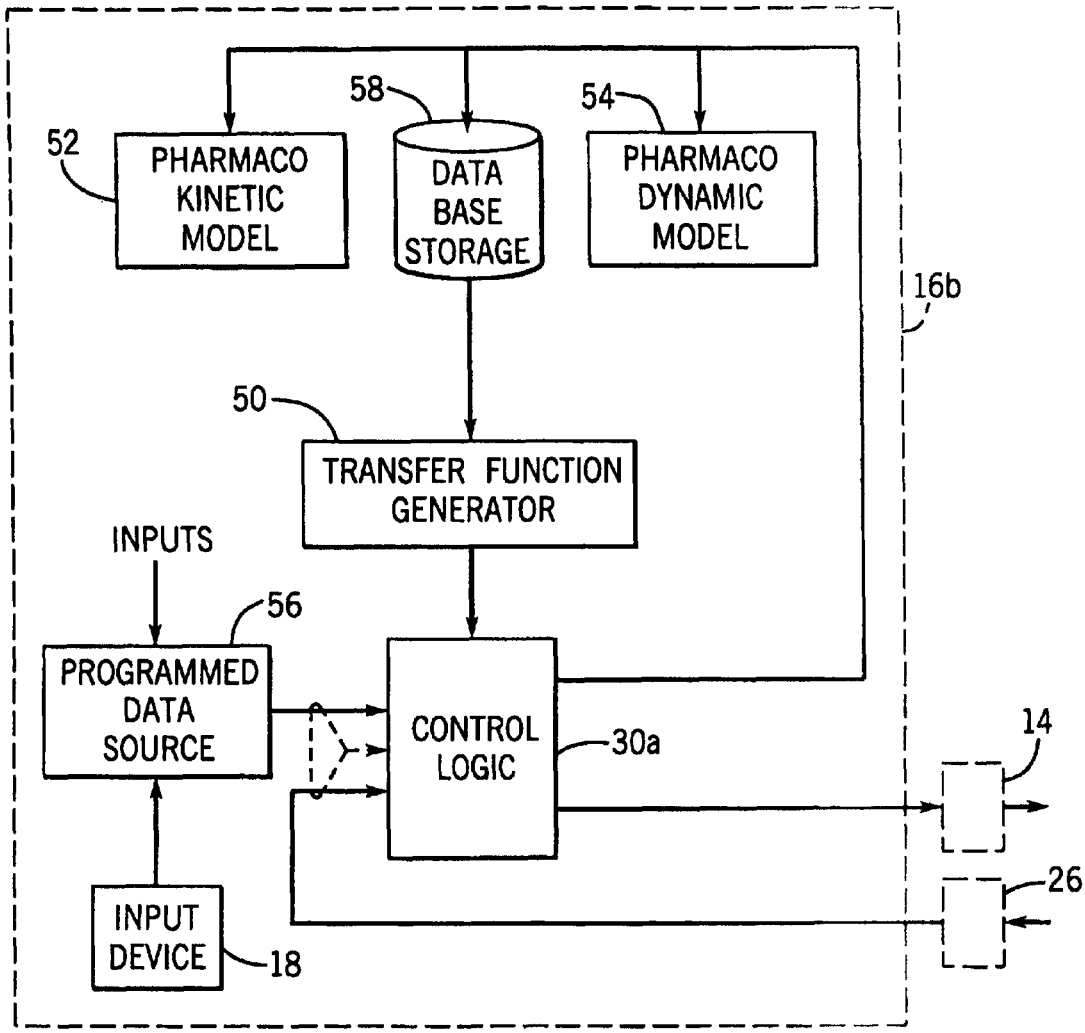
FIG. 4 is another schematic diagram showing a further modification of the control shown in FIG. 1.

FIG. 4 shows a modification of the control unit for the closed loop control apparatus shown in FIG. 1. As noted above, the pharmacology resulting from the administration of a drug depends to a considerable extent on the pharmacodynamic and pharmacokinetic properties of the drug. This is particularly true of a hypnotic drug that is not delivered directly into the effect-site. That is, an intravenously supplied hypnotic drug, such as propofol, is delivered to the venous blood of the patient whereas its effect occurs in the brain. For an inhaled drug that is delivered to the respiratory tract of the patient, somewhat more information is available as the concentration of the gas in the lung, which can be measured, is in steady state proportional to the concentration in arterial blood. Therefore, less pharmacokinetic modeling is required as the blood compartment concentration can be obtained from measurements.

In the embodiment of the invention schematically shown in FIG. 4, a transfer function generator 50 may be used to improve the drug administration by control 10. Transfer function generator 50 establishes a desired relationship between the measured hypnotic level in patient 12, as characterized by the degree of complexity in the EEG signal data, and the rate or other characteristics of drug administration by anesthetic delivery unit 14. It also establishes a relationship between EEG signal data complexity and the clinical endpoints of hypnosis levels. In establishing the transfer function, a pharmacokinetic model 52 and pharmacodynamic model 54 for the drug may be employed. These models typically comprise algorithms describing the interaction between the hypnotic drug and a patient stored in, and employed by, a computer. The output of transfer function generator 50 is provided to control logic 30a in control unit 16b for use in its operation in the provision of an output signal to anesthetic delivery unit 14. For this purpose, control unit 16b, in addition to a comparative function, may comprise other control or computational elements, such as microprocessors, in control logic 30a. Control logic 30a may provide data, such as the state of its regulation, regulatory routines, or the various signal magnitudes in control unit 16b to models 52 and 54. In cases where a volatile hypnotic drug has been administered to the patient either alone or in addition to an intravenous drug, its concentration, as determined by the end tidal fraction $ET_{conc}$, may be provided to control unit 16b and to pharmacokinetic model [54] *52* to permit less complicated pharmacokinetic modeling. Cardiovascular parameter data may also be provided to one or more of the models to improve the operation of the models and control 10 and patient safety.

Pharmacokinetic model 52 allows the hypnotic drug to be administered in such a way that its relative concentration in a given compartment, i.e. the brain, can be maintained generally stable, or constant at that which produces the desired hypnotic level. This stability brings a major advantage for both the patient and the anesthesiologist since once an efficient level of drug effect has been reached, the drug level, and hence the hypnotic level will remain constant, thereby to avoid changes in the patient condition, such as regaining consciousness. However, since an hypnotic drug's real effect cannot be fully predicted for a given patient due to pharmacogenetics and because of the variability among individuals of pharmacokinetics models, the use of pharmacodynamic model 54, in addition to pharmacokinetic model 52 and the determination of EEG signal data complexity by unit 26 allows for both the determination of the appropriate effect-site concentration, i.e. the concentration to achieve a given hypnotic level and hence EEG signal data complexity level, as well as a steady state drug level. Where needed for both the models, the "effect" of the hypnotic drug can be measured by evaluating the complexity of the EEG signal data, particularly that originating from the cerebral portion of the EEG signal data.

Also, as shown in FIG. 4, a programmed data source 56 can be provided in control unit 16b for use in operation of control 10. In addition to the input relating to the hypnotic level, source 56 may be used to generate and input data specific to a given anesthetization, including the patient's anthropometrics, such as weight, age, height, sex, body mass index, and the like. The data may also include information identifying the drug that is being administered to the patient. Other data that may be entered at source 56 include information pertaining to the duration of the procedure, the intensity of the surgery, minimum and maximum drug administration levels and/or rates, upper and lower hypnosis level limits and cardiovascular parameters, and the like. Such data could also include information regarding the pattern of surgical intensity likely to be encountered by the patient according to the type of surgery and/or the technique to be employed by the surgeon, and the idiosyncrasies of the surgical practice of a given surgeon. Information of this and other types can be inputted on an individual basis by an anesthesiologist or stored and retrieved from a database of preset surgical information. Such information may also be provided to models 52 and 54, via control logic 30a for use in their operation.

Programmed data in source 56 may also include timing data. This data may be used by control unit 16b to establish a stable, set complexity level for the EEG data signal, and hence hypnotic level in patient 12, for a predetermined period of time. Or, the programmed data may be such that the anesthesiologist could operate program data source [58] *56* so that control 10 is operated in a manner to wake the patient after a preset time as for example, by setting up a "wake-up after ten minutes" routine in source 56. Responsive to inputs provided from data source 56, control logic 30a would then establish the required drug administration rates and timing for anesthetic delivery unit 14 to patient 12 to obtain this effect and timing. An analogous procedure could be carried out with respect to the administration of the hypnotic drug to induce unconsciousness, i.e. loss of consciousness in patient 12 at a point in time in the future. Such features are advantageous for cost savings in terms of operating room usage times, amounts of drug used, and the like.

The transfer function generator 50, as well as models 52, 54, may be supplied with information from a database storage device 58. Such a storage device will typically retain reusable data, such as standard data or stored patient data inputted to the storage device or inputted, or developed by control 10. This will enable patient data obtained during a prior anesthetization to be reused should the patient require a subsequent anesthetization with the same drug. If desired, transfer function generator [58] *50* may also store information of the type described above in connection with source 56, such as patient type, nature of the surgery, surgical intensity, patterns, drug interaction, etc.

Also, control 10 can record a time series of measured and computed patient information to compute, after enough data is recorded, a patient's specific profile that, thereafter, can be used to predict the behavior of the patient for any particular change of drug delivery rate, as by use of models 52 and 54.

It will be appreciated that, for safety reasons, the control will include appropriate means to allow the anesthesiologist to manually control the delivery of the hypnotic agent, by operation of an input device, by direct intervention at the anesthetic delivery unit, or in same other effective manner.

It is recognized that other equivalents, alternatives, and modifications aside from those expressly stated, are possible and within the scope of the appended claims.

What is claimed is:

1. A method for administering an hypnotic drug to a patient *to establish a desired hypnotic level in the patient*, said method comprising the steps of:

(a) establishing a *reference signal corresponding to the* desired hypnotic level to be [provided] *established* in the patient *from the administration of the hypnotic drug*;

(b) administering the hypnotic drug to the patient;

(c) obtaining EEG signal data *resulting* from *cerebral activity of* the patient *and obtaining EMG signals resulting from muscle activity of the patient*;

(d) deriving at least one measure of the complexity *characteristics* of the EEG signal data;

(e) *deriving a measure of patient EMG activity;*

(*f*) determining the hypnotic level existing in the patient from the complexity *characteristics* of the EEG signal data *combined with the derived measure of patient EMG activity and providing a feedback signal corresponding to the hypnotic level existing in the patient*;

[(f)] (*g*) comparing the *feedback signal corresponding to the* hypnotic level existing in the patient *as a result of the administration of the hypnotic drug* to *the reference signal corresponding to* the desired hypnotic level *to be established in the patient from the administration of the drug to produce a control signal, indicative of the difference between the desired hypnotic level and the existing hypnotic level*; and

[(g)] (*h*) controlling the [administration] *amount* of the hypnotic drug *administered* to the patient in accordance with the [comparison of step (f)] *control signal so that the hypnotic level of the patient is established and maintained at that corresponding to the reference signal*.

2. The method according to claim 1 wherein step (d) is further defined as measuring an entropy of the EEG signal data.

3. The method according to claim 2 wherein step (d) is further defined as measuring the spectral entropy of the EEG signal data.

4. The method according to claim 2 wherein step (d) is further defined as measuring the approximate entropy of the EEG signal data.

5. The method according to claim 1 wherein step (d) is further defined as employing a Lempel-Ziv complexity measure.

6. The method according to claim 1 wherein step (d) is further defined as carrying out a fractal spectrum analysis to measure the complexity *characteristics* of the EEG signal data.

7. The method according to claim 1 further defined as deriving a plurality of EEG signal data complexity *characteristics* measures for use in determining the hypnotic level of the patient [and controlling the administration of the hypnotic drug to the patient].

[8. The method according to claim 1 wherein step (c) is further defined as obtaining EEG signals resulting from the cerebral activity of the patient for use in the derivation of the measure of step (d).]

[9. The method according to claim 8 wherein step (c) is further defined as obtaining EMG signals resulting from the muscle activity of the patient and the method further includes the step of deriving a measure of patient EMG activity for use with the derived measure of EEG signal complexity in controlling the administration of the hypnotic drug to the patient.]

10. The method according to claim [9] *1* wherein the step of deriving the measure of patient EMG activity is further defined as deriving the measure from a frequency domain power spectrum of the EMG signals.

11. The method according to claim [8] *1* wherein [step (c) is further defined as obtaining EMG signals resulting from the muscle activity of the patient and] step (d) further includes the step of deriving a measure of the complexity *characteristics* of EEG signal data over a frequency spectrum incorporating [the] EEG signals and EMG signals for use with [the] *a* derived measure of the EEG signal *data* complexity [in controlling the administration of the hypnotic drug to the patient] *characteristics*.

12. The method according to claim 1 further including the steps of establishing desired cardiovascular characteristics for the patient; obtaining cardiovascular data from the patient; comparing the cardiovascular data of the patient to desired cardiovascular characteristics; and further controlling the administration of the hypnotic drug in accordance with the comparison of cardiovascular characteristics and data.

13. The method according to claim 1 further including the step of establishing a transfer function between the pharmacological effects of the hypnotic drug in the patient and the administration of the drug to the patient for use in controlling the *hypnotic* drug administration.

14. The method according to claim 1 further including the step of employing a pharmacokinetic model in controlling the administration of the *hypnotic* drug to the patient.

15. The method according to claim 1 further including the step of employing a pharmacodynamic model in controlling administration of the *hypnotic* drug to the patient.

16. The method according to claim 15 further including the step of employing a pharmacokinetic model in controlling the administration of the *hypnotic* drug to the patient.

17. The method according to claim 13 further including the step of employing a pharmacokinetic model in establishing the transfer function for *use in* controlling the administration of the *hypnotic* drug to the patient.

18. The method according to claim 13 further including the step of employing a pharmacodynamic model in establishing the transfer function for *use in* controlling administration of the *hypnotic* drug to the patient.

19. The method according to claim 17 further including the step of employing a pharmacodynamic model in establishing the transfer function for *use in* controlling administration of the *hypnotic* drug to the patient.

20. The method according to claim 1 further including the step*s* of measuring amounts of volatile hypnotic [drugs] *drug* in *the exhaled* breathing gases [in] *of* the patient and controlling the administration of the hypnotic [drugs] *drug* in accordance with the volatile drug measurement.

21. The method according to claim 13 further including the step*s* of measuring amounts of volatile hypnotic [drugs] *drug* in *the exhaled* breathing gases [in] *of* the patient and [as] employing the measurement in establishing the transfer function for use in controlling the administration of the *hypnotic* drug.

22. The method according to claim 13 further including the steps of obtaining cardiovascular data from the patient and [as] employing the cardiovascular data in establishing the transfer function for use in controlling the administration of the hypnotic drug.

23. The method according to claim 1 further including the step of providing information relating to one or more of the patient, the hypnotic drug, a medical procedure, and a physician for use in controlling the administration of the hypnotic drug to the patient.

24. The method according to claim 1 further including the step of storing information relating to one or more of the patient, the hypnotic drug, a medical procedure, and a physician for use in controlling the administration of the hypnotic drug to the patient.

25. The method according to claim 24 wherein the stored information includes information relating to a previous anesthetization of the patient.

26. The method according to claim 23 further including the step of storing information relating to one or more of the patient, the hypnotic drug, a medical procedure, and a physician [and as employing the stored information] *for use* in controlling the administration of the hypnotic drug to the patient.

27. The method according to claim 1 including the step*s* of generating information in the course of an anesthetization and employing the generated information in controlling the administration of the hypnotic drug to the patient.

28. Apparatus for administering an hypnotic drug to a patient *to establish a desired hypnotic level in the patient*, said apparatus comprising:

(a) means for establishing a *reference* signal corresponding to [a] *the* desired hypnotic level [for] *to be established* in the patient *from the administration of the hypnotic drug*;

(b) an anesthetic delivery unit for administering the hypnotic drug to the patient;

(c) [a] sensor *means* for obtaining EEG signal data *resulting* from the *cerebral activity of the* patient *and for obtaining an EMG signal resulting from muscle activity of the patient*;

(d) means coupled to said sensor *means* for deriving at least one measure of the complexity *characteristics* of the EEG signal data *and for deriving a measure of EMG activity from the EMG signal*, for determining the hypnotic level existing in the patient from the complexity *characteristics* of the EEG signal data *combined with the derived measure of EMG activity*, and for providing a *feedback* signal corresponding to [same] *the hypnotic level existing in the patient*; and (e) a control unit including a comparator having inputs coupled to said elements (a) and [(c)] (*d*) and an output coupled to element (b), said comparator comparing the [signals] *feedback signal* corresponding to the hypnotic level existing in the patient *as a result of the administration of the hypnotic drug* and the *reference* signal corresponding to the desired hypnotic level *to be established in the patient from the administration of the drug* and providing an output signal *to the anesthetic delivery unit, indicative of the difference between the reference and feedback signals,* for controlling the anesthetic delivery unit and the [administration] *amount* of the hypnotic drug *administered to the patient by the anesthetic delivery unit* in accordance with the [comparison] *output signal so that the hypnotic level of the patient is established and maintained at that corresponding to the reference signal*.

29. The apparatus according to claim 28 wherein element (d) is further defined as means for measuring an entropy of the EEG *signal* data to [determine the hypnotic level existing in the patient] *derive at least one measure of the complexity characteristics of the EEG signal data*.

30. The apparatus according to claim 29 wherein element (d) is further defined as means for measuring the spectral entropy of the EEG signal data.

31. The apparatus according to claim 29 wherein element (d) is further defined as means for measuring the approximate entropy of the EEG signal data.

32. The apparatus according to claim 28 wherein element (d) is further defined as means employing a Lempel-Ziv complexity measure to [determine the hypnotic level existing in the patient] *derive at least one measure of the complexity characteristics of the EEG signal data*.

33. The apparatus according to claim 28 wherein element (d) is further defined as means for carrying out a fractal spectrum analysis to measure the complexity *characteristics* of the EEG signal data [to determine the hypnotic level existing in the patient].

34. The apparatus according to claim 28 wherein element (d) is further defined as deriving a plurality of EEG signal data complexity *characteristics* measures [for determining the hypnotic level existing in the patient] *to derive at least one measure of the complexity characteristics of the EEG signal data*.

[35. The apparatus according to claim 28 wherein element (c) is further defined as a sensor for obtaining EEG signals resulting from the cerebral activity of the patient and element (d) is further defined as using EEG signals in providing the signal corresponding to the hypnotic level existing in the patient.]

[36. The apparatus according to claim 35 wherein element (c) is further defined as a sensor for obtaining EMG signals resulting from the muscle activity of the patient and element (d) is further defined as deriving a measure of EMG activity from the EMG signals and using same with a measure derived from EEG signal complexity to provide the signal corresponding to the hypnotic level in the patient.]

37. The apparatus according to claim [36] *28* wherein element (d) is further defined as means for obtaining a frequency domain power spectrum of the EMG [signals] *signal* to derive the measure of EMG activity in the patient.

38. The apparatus according to claim [35] *37* wherein [element (c) is further defined as a sensor for obtaining EMG signals resulting from the muscle activity of the patient and] element (d) is further defined as means for deriving the complexity *characteristics* of the EEG signal data over a frequency spectrum incorporating the EEG [signals] *signal data* and EMG [signals] *signal* for use with a derived measure of EEG signal *data* complexity *characteristics* to determine the hypnotic level of the patient.

39. The apparatus according to claim 28 further including means for providing a signal corresponding to desired cardiovascular characteristics for the patient; means for obtaining cardiovascular signal data from the patient; means for comparing the cardiovascular signal data of the patient to *the* desired cardiovascular characteristic*s* signal; and means for controlling the anesthetic delivery unit and the administration of the hypnotic drug in accordance with the comparison of the cardiovascular characteristics signal and cardiovascular signal data.

40. The apparatus according to claim 28 further including means in said control unit for establishing a transfer function between [the] pharmacological effects in the patient and the administration of the *hypnotic* drug to the patient for use in controlling said anesthetic delivery unit.

41. The apparatus according to claim 28 further including pharmacokinetic model means in said control unit for use in controlling operation of said anesthetic delivery unit.

42. The apparatus according to claim 28 further including pharmacodynamic model means in said control unit for use in controlling operation of said anesthetic delivery unit.

43. The apparatus according to claim 42 further including pharmacokinetic model means in said control unit for use in controlling the operation of said anesthetic delivery unit.

44. The apparatus according to claim 40 further including pharmacokinetic model means for use with said transfer function *establishing* means in controlling the operation of said anesthetic delivery unit.

45. The apparatus according to claim 40 further including pharmacodynamic model means in said control unit for use with said transfer function *establishing* means in controlling the operation of said anesthetic delivery unit.

46. The apparatus according to claim 44 further including pharmacodynamic model means in said control unit for use with said transfer function *establishing* means in controlling the operation of said anesthetic delivery unit.

47. The apparatus according to claim 28 further including means for measuring amounts of volatile hypnotic [drugs] *drug* in the *exhaled* breathing gases [in] *of* the patient and coupled to said control unit for use in controlling the anesthetic delivery unit.

48. The apparatus according to claim 40 further including means for measuring amounts of volatile hypnotic [drugs] *drug* in the *exhaled* breathing gases [to] *of* the patient, said means being coupled to said transfer function *establishing* means for use in establishing the transfer function.

49. The apparatus according to claim 40 further including means for obtaining cardiovascular data from the patient, said means being coupled to said transfer function *establishing* means for use in establishing the transfer function.

50. The apparatus according to claim 28 further including means for providing information relating to one or more of the patient, the hypnotic drug, a medical procedure, and a physician for use in controlling the administration of the hypnotic drug to the patient.

51. The apparatus according to claim [50] *28* further including storage means for storing information relating to one or more of the patient, the hypnotic drug, a medical procedure, and a physician for use in controlling the administration of the hypnotic drug to the patient.

52. The apparatus according to claim 51 wherein the storage means stores information relating to a previous anesthetization of the patient.

53. The apparatus according to claim 50 further including storage means for storing information relating to one or more of the patient, the hypnotic drug, a medical procedure, and a physician for use in controlling the administration of the hypnotic drug to the patient.

54. The apparatus according to claim 28 including means for generating information in the course of an anesthetization and for employing the generated information in controlling the administration of the hypnotic drug to the patient.

* * * * *